United States Patent [19]

Winn et al.

[11] 4,171,367
[45] Oct. 16, 1979

[54] PYRAZOLYL AMINO IMIDAZOLINES

[75] Inventors: Martin Winn, Deerfield; Carl W. Nordeen, Waukegan, both of Ill.

[73] Assignee: Abbott Laboratories, North Chicago, Ill.

[21] Appl. No.: 770,137

[22] Filed: Feb. 18, 1977

[51] Int. Cl.² .................. A61K 31/415; C07D 403/12
[52] U.S. Cl. ............................. 424/273 P; 548/316; 548/358; 548/362; 548/376
[58] Field of Search ................ 548/316, 348; 424/273

[56] References Cited

U.S. PATENT DOCUMENTS

| | | | |
|---|---|---|---|
| 3,530,140 | 9/1970 | Kummer et al. | 548/348 |
| 3,954,757 | 5/1976 | Arya et al. | 548/348 |
| 3,979,408 | 9/1976 | Trani | 548/316 |
| 4,108,982 | 8/1978 | Amschler | 548/316 |

OTHER PUBLICATIONS

Clark et al. Chem. Abst. 1974, vol. 81, No. 49614q.
Crenshaw et al. J. Med. Chem. 1976, vol. 19, pp. 262–267, 274 & 275.
Senga et al. Chem. Abst. 1976, vol. 84, No. 59372k.
Pollak et al., Monatshefte fur Chemie 1972, vol. 103, pp. 1591–1603.
Verge et al., Chem. Abst. 1975, vol. 83, No. 10079k.

*Primary Examiner*—Natalie Trousof
*Attorney, Agent, or Firm*—Robert L. Niblack; Gildo E. Fato

[57] ABSTRACT

Described are compounds of the formula

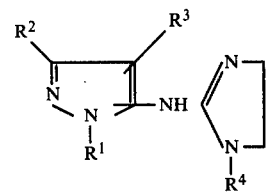

wherein $R^1$ and $R^2$ are hydrogen, alkyl, cycloalkyl, and aryl, $R^3$ is hydrogen or halogen, and $R^4$ is hydrogen or acyl, and pharmaceutically acceptable acid addition salts thereof. $R^3$ can be located in the 4 or 5 position as can the amino imidazoline group. The compounds are useful as anti-inflammatory agents.

12 Claims, No Drawings

PYRAZOLYL AMINO IMIDAZOLINES

BACKGROUND OF THE INVENTION

Rheumatic conditions affect humans and animals, these conditions involving swelling, decreased mobility, tenderness, pain, and fever. While anti-inflammatory agents are presently available which are effective in symptomatic treatment of conditions such as degenerative joint diseases, rheumatoid arthritis, rheumatoid spondylitis, and the like, such agents are not entirely effective in stopping the progression of the disease. The availability of additional anti-inflammatory agents is therefore desirable. The present invention provides a number of such anti-inflammatory agents.

DETAILED DESCRIPTION

This invention relates to compounds represented by the formula

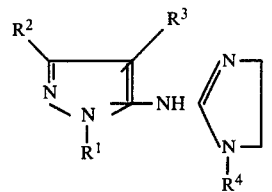

wherein $R^1$ and $R^2$ are hydrogen, alkyl, cycloalkyl, and aryl, $R^3$ is hydrogen or halogen, and $R^4$ is hydrogen or acyl. $R^3$ can be located in the 4 or 5 position on the pyrazole ring as can the amino imidazoline group. The term "alkyl" includes one to six carbon atoms. Within this group of compounds are included those in which $R^1$ is methyl or phenyl, $R^2$ is hydrogen, methyl or propyl, $R_3$ is hydrogen, chloro, bromo, or iodo and $R^4$ is hydrogen or acetyl.

The compounds of this invention exhibit anti-inflammatory activity and are generally administered to mammalian patients in dosages of from about 5 to 200 milligrams per kilogram (mg/kg) of body weight daily, either in single or divided doses over a 24 hour period.

The compounds of the present invention can be prepared by several methods, as illustrated below.

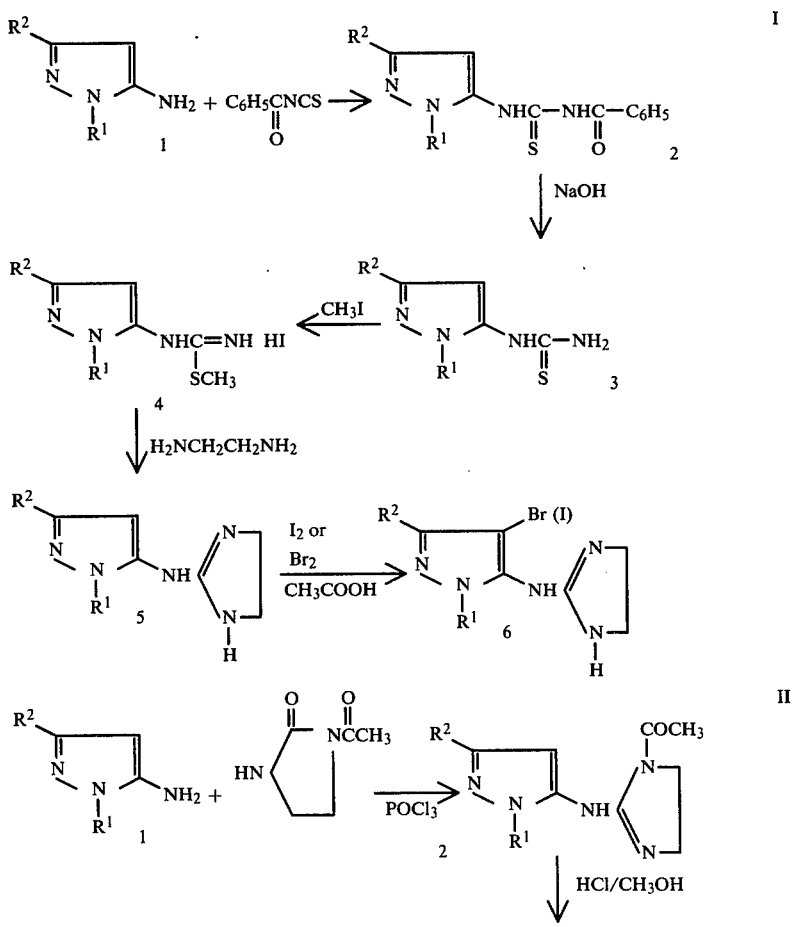

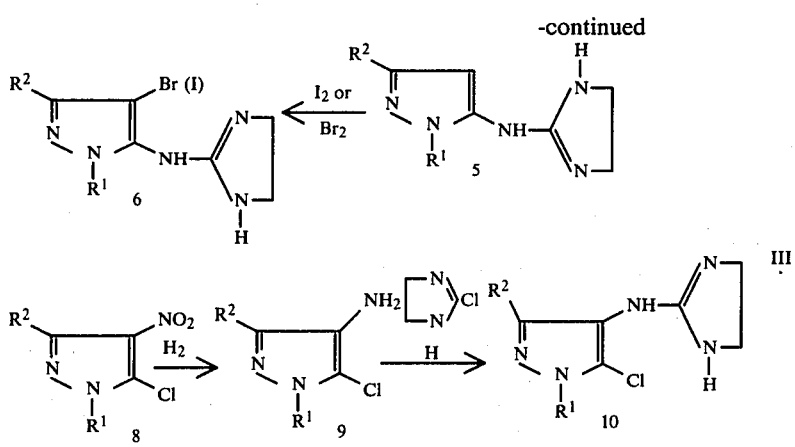

In the first method a 1,3-disubstituted-5-aminopyrazole (1) is reacted with benzoyl isothiocyanate to produce N(1,3-disubstituted-5-pyrazolyl)-N[1]-benzoyl thiourea (2). This products reacts with sodium hydroxide to produce (1,3-disubstituted-5-pyrazolyl) thiourea (3) which in turn reacts with methyl iodide to produce N(1,3-disubstituted-5-pyrazolyl)-5-methyl isothiourea hydroiodide (4). This compound then reacts with ethylene diamine to produce 2-(1,3-disubstituted-5-pyrazolyl)amino-2-imidazoline (5), which is treated with a halogen (Br$_2$ or Ir) to produce 2(4-Halo-1,3-disubstituted-5-pyrazolyl)amino-2-imidazoline.

In the second method, compound (1) is reacted with 1-acetyl-2-imidazolidinone to produce 1-acetyl-2-(1,3-disubstituted 5-pyrazolyl)amino-2-imidazoline (7). The acetyl group is removed with HCl in methanol to produce the compound 5 which is halogenated as above to produce compound 6.

In the third method, a 1,3-disubstituted-5-chloro-4-nitro pyrazole (8) is hydrogenated to 1,3-disubstituted-5-chloro-4-amino pyrazole (9) which reacts with 2-chloro-2-imidazoline to produce 2(1,3-disubstituted-5-chloro-4-pyrazolyl)amino-2-imidazoline (10).

The preferred method of preparation is represented by the second method, described above. Representative compounds which can be prepared are exemplified in the following examples.

EXAMPLE I

1-Acetyl-2(3-isopropyl-1-methyl-5-pyrazolyl)amino-2-imidazoline 5-amino-3-isopropyl-1-methyl pyrazole (described in British Pat. No. 1,057,740) (19.3 g) was dissolved in 180 ml. phosphorus oxychloride (POCl$_3$). 1-Acetyl-2-imidazolidinone (J. Chem Soc 1964, 178) (20.1 g) was added. This reaction mixture was stirred at 55° for 40 hr. The solvents were concentrated in vacuum, ice and methylene chloride were added and the mixture neutralized with 25% sodium hydroxide in water. The methylene chloride layer was dried over MgSO$_4$ and then concentrated and the residue crystallized from isopropyl alcohol and ether to give 12.73 g. of product, mp 145°–147° C.

EXAMPLE II

2(3-Isopropyl-1-methyl-5-pyrazolyl)-amino-2-imidazoline

1-Acetyl-2(3-isopropyl-1-methyl-5-pyrazolyl)-amino-2-imidazoline (6.21 g.), 120 ml. methanol and 2 drops concentrated hydrochloric acid were mixed and refluxed 16 hr. The solution was then concentrated and the residue treated with CHCl$_3$ and KHCO$_3$ solution. The CHCl$_3$ solution was dried over MgSO$_4$, concentrated and the residue crystallized from isopropyl alcohol and ether to give 4.50 g. of product, mp 163°–165° C.

Analyzed for C$_{10}$H$_{17}$N$_5$: theoretical; C=57.94, H=8.28, N=33.79 Found; C=57.83, H=8.45, N=33.58.

EXAMPLE III

2(4-Bromo-3-isopropyl-1-methyl-5-pyrazolyl)amino-2-imidazoline hydrobromide

2(3-isopropyl-1-methyl-5-pyrazolyl)-amino-2-imidazoline (6.00 g.) was dissolved in 30 ml. acetic acid. A solution of 4.55 g. bromine in 10 ml. acetic acid was added dropwise, while cooling, until the color of Br$_2$ persisted. The solution was concentrated in vacuum and the residue crystallized from isopropyl alcohol to give 7.85 g. product, mp 225°–226° C., decomposed.

Analyzed for C$_{10}$H$_{17}$Br$_2$N$_5$: Theoretical; C=32.72, H=4.66, N=19.07 Found; C=32.78, H=4.72, N=19.24.

EXAMPLE IV

[1-(3-Methylbutyl)-3-methyl-5-pyrazolyl]thiourea 1-(3-methylbutyl)-3-methyl-5-aminopyrazole (British Pat. No. 1,057,740) (21.2 g.) was dissolved in 560 ml. benzene. Benzoyl isothiocyanate (21.19 g.) was added dropwise and then the solution was refluxed for 1 hr. The solvent was evaporated in vacuum to yield the intermediate benzoyl pyrazolyl thiourea. This compound was hydrolyzed by refluxing in 100 ml. 10% sodium hydroxide for 20 minutes. Then the mixture was cooled and acidified to a pH of 4 with hydrochloric acid. The resulting solid was filtered, washed with water, and then treated with concentrated ammonia. After stirring 5 minutes the solid was filtered, washed with water, and crystallized from an ethanol-hexane mixture to give 23.0 g. product, mp 173°–176° C.

EXAMPLE V

N[1(3-Methylbutyl)-3-methyl-5-pyrazolyl]-S-methyl isothiourea hydroiodide

[1-(3-methylbutyl)-3-methyl-5-pyrazolyl]thiourea (23.0 g.) was dissolved in 250 ml. ethanol and 15.62 g. methyl iodide and refluxed for 4 hours. The ethanol was concentrated in vacuum and ether added to get 29.3 g. product, mp 128°–131° C.

EXAMPLE VI

2[1-(3-Methylbutyl)-3-methyl-5-pyrazolyl]amino-2-imidazoline

N[1-(3-methylbutyl)-3-methyl-5-pyrazolyl]-S-methyl isothiourea hydroiodide (29.0 g.) was suspended in 160 ml. n-propyl alcohol. Ethylene diamine (10.2 g.) was added and the solution was refluxed 18 hrs. The solvent was concentrated in vacuum and the residue was treated with $KHCO_3$ in water. The resulting solid was recrystallized from $CHCl_3$-ether mixtures to obtain 14.3 g. product, mp 104°–106° C.

Analyzed for $C_{12}H_{21}N_5$: Theoretical; C=61.24, H=9.03, N=29.76, Found; C=61.40, H=9.33, N=29.69.

EXAMPLE VII

2[4-Bromo-1-(3-methylbutyl)-3-methyl-5-pyrazolyl]amino-2-imidazoline hydrochloride 2[1-(3-methylbutyl)-3-methyl-5-pyrazolyl]amino-2-imidazoline (6.00 g.) in 35 ml. acetic acid was treated with a solution of 4.10 g. bromine in 10 ml. acetic acid, added dropwise, the solution was then concentrated and the residue treated with chloroform, water, and potassium bicarbonate. The $CHCl_3$ phase was dried over $MgSO_4$ and concentrated. The residue was dissolved in isopropyl alcohol and acidified with HCl. On adding ether, 7.06 g. product, mp 180°–182° C. crystallized out.

Analyzed for $C_{12}H_{21}BrClN_5$: Theoretical; C=41.15, H=6.03, N=19.98 Found; C=41.19, H=6.61, N=20.33.

EXAMPLE VIII

1-Acetyl-2-(1-phenyl-5-pyrazolyl)-amino-2-imidazoline.

5-Amino-1-phenylpyrazole (6.00 g.), and 1-acetyl-2-imidazolidinone (5.50 g.) were reacted as described in Example I to give 4.95 g. of product, mp 157°–159° C.

Analyzed for $C_{14}H_{15}N_5O$: Theoretical; C=60.40, H=5.85, N=25.11 Found; C=60.65, H=5.74, N=24.75.

EXAMPLE IX 2-(1-Phenyl-5-pyrazolyl)-amino-2-imidazoline

Acetyl-2(1-phenyl-5-pyrazolyl)-amino-2-imidazoline (15.1 g.) was treated with HCl in methanol as described in Example II to give 12.5 g. product mp 206°–208° C. The hydrochloride, made with HCl in isopropyl alcohol had a mp of 232°–234° C.

Analyzed for $C_{12}H_{14}ClN_5$: Theoretical; C=54.70, H=5.36, N=26.55 Found: C=54.91, H=5.41, N=26.69.

EXAMPLE X 2-(4-Bromo-1-phenyl-5-pyrazolyl)-amino-2-imidazoline hydrochloride 2-(1-phenyl-5-pyrazolyl)-amino-2-imidazoline (5.00 g.) and 3.85 g. bromine were reacted as described in Example VII to give 6.02 g. of product, mp 251°–253° C.

Analyzed for $C_{12}H_{13}BrClN_5$: Theoretical; C=42.02, H=3.83, N=20.50 Found; C=42.21, H=3.85, N=19.81.

EXAMPLE XI

1-Acetyl-2(1-isopropyl-3-methyl-5-pyrazolyl)amino-2-imidazoline 5-amino-1-isopropyl-3-methylpyrazole (J. Gen. Chem. USSR 31 234, 1961) (19.3 g.) and 1-acetyl-2-imidazolidinone (20.1 g.) were reacted as described in Example I to give 12.73 g. of product, mp 145°–147° C.

EXAMPLE XII 2-(1-Isopropyl-3-methyl-5-pyrazolyl)amino-2-imidazoline 1-acetyl-2-(1-isopropyl-3-methyl-5-pyrazolyl)amino-2-imidazoline (14.0 g.) was treated with HCl in methanol as described in Example II to give 9.05 g of product, mp 173°–175° C.

Analyzed for $C_{10}H_{17}N_5$: Theoretical; C=57.94, H=8.28, N=33.79 Found; C=57.76, H=8.44, N=33.93

EXAMPLE XIII 2-(4-Bromo-1-isopropyl-3-methyl-5-pyrazolyl)amino-2-imidazoline hydrochloride 2-(1-isopropyl-3-methyl-5-pyrazolyl)amino-2-imidazoline (6.00 g.) was treated with 4.60 g. of bromine as described in Example VII to give 8.26 g. product, mp 235°–256° C.; decomposed.

Analyzed for $C_{10}H_{17}ClBrN_5$: Theoretical; C=37.21, H=5.32, N=21.70 Found; C=37.17, H=5.26, N=21.62.

EXAMPLE XIV 2-(1-Cyclohexyl-5-pyrazolyl)-amino-2-imidazoline 2-(1-phenyl-5-pyrazolyl)-amino-2-imidazoline (9.00 g.) in 250 ml. methanol was hydrogenated at 3 atmospheres and 60° C. over 5% $Rh/Al_2O_3$ catalyst. The catalyst was filtered, the solvent removed in vacuum and the residue crystallized from benzene to give 4.0 g. of product, mp 183°–185° C.

Analyzed for $C_{12}H_{19}N_5$: Theoretical; C=61.78, H=8.21, N=30.02 Found; C=61.63, H=8.33, N=29.63.

EXAMPLE XV 2-(4-Bromo-1-cyclohexyl-5-pyrazolyl)-amino-2-imidazoline hydrochloride 2-(1-cyclohexyl-5-pyrazolyl)-amino-2-imidazoline (6.40 g.) was treated with 14.30 g bromine as described in Example VII to give 8.10 g. product, mp 242°–244° C. decomposed.

Analyzed for $C_{12}H_{19}BrClN_5$: Theoretical; C=41.30, H=5.49, N=20.08 Found, C=41.18, H=5.09, N=19.65.

EXAMPLE XVI

5-Amino-1,3-di-isopropyl pyrazole 4-methyl-3-keto pentanitrile (13.0 g) Can. J. Chem. 48, 2110, 1970) (13.0 g.), isopropyl hydrazine (10.0 g.) and 50 ml. ethanol were refluxed for 4 hrs. The solvent was removed in vacuum and the residue crystallized from cyclohexane and ether to produce 13.88 g. of product, mp 62°–65° C.

Analyzed for $C_9H_{17}N_3$: Theoretical; C=64.63, H=10.25, N=25.13 Found; C=64.67, H=10.51, N=25.40

EXAMPLE XVII

1-Acetyl-2-(1,3-di-isopropyl-5-pyrazolyl)amino-2-imidazoline 5-Amino-1,3-di-isopropyl pyrazole (13.5 g.) and 1-acetyl-2-imidazolidinone (12.2 g.) were reacted as described in Example I to give 13.01 g. of product, mp 139°–140° C.

EXAMPLE XVIII 2-(1,3-Di-isopropyl-5-pyrazolyl)-amino-2-imidazoline

1-Acetyl-3-(1,3-di-isopropyl-5-pyrazolyl)amino-2-imidazoline (13.0 g.) was treated with HCl in methanol as described in Example II to give 6.60 g. of product, mp 159°–161° C.

Analyzed for $C_{12}H_{21}N_5$: Theoretical; C=61.24, H=9.00, N=29.76 Found; C=61.04, H=9.21, N=29.93.

EXAMPLE XIX 2-(4-Bromo-1,3-di-isopropyl-5-pyrazolyl)amino-2-imidazoline hydrobromide 2-(1,3-Di-isopropyl-5-pyrazolyl)-amino-2-imidazoline (2.00 g.) was treated with 1.5 g. bromine as described in Example III to give 2.61 g. of product, mp 220°–221° C., decomposed.

Analyzed for $C_{12}H_{21}Br_2N_5$: Theoretical; C=36.47, H=5.35, N=17.73, Br=40.45 Found; C=36.71, H=5.56, N=17.60, Br=40.36.

EXAMPLE XX (1,3-Diphenyl-5-pyrazolyl) thiourea 1,3-Diphenyl-5-amino pyrazole (117.5 g.) and benzoyl isothiocyanate (89.65 g.) were reacted as described in Example IV to give 119.8 g. of product, mp 198°–201° C.

EXAMPLE XXI

N-(1,3-Diphenyl-5-pyrazolyl)-S-methyl isothiourea hydroiodide (1,3-Diphenyl-5-pyrazolyl) thiourea (119.7 g.) and 63.9 g. methyl iodide were reacted as described in Example V to give 156.1 g. of product, mp 178°–182° C.

EXAMPLE XXII

2(1,3-Diphenyl-5-pyrazolyl) amino-2-imidazoline

N(1,3-Diphenyl-5-pyrazolyl)-S-methyl isothiourea hydroiodide (43.6 g.) and ethylene diamine (12.0 g.) were reacted as described in Example VI to give 26.0 g. of the product, mp. 228°–230° C.

Analyzed for $C_{18}H_{17}N_5$: Theoretical; C=71.29, H=5.61, N=23.10 Found; C=71.20, H=5.64, N=23.16.

EXAMPLE XXIII

2(4-Bromo-1,3-diphenyl-5-pyrazolyl) amino-2-imidazoline hydrobromide

2(1,3-diphenyl-5-pyrazolyl) amino-2-imidazoline (6.0 g.) was treated with 3.2 g. bromine as described in Example III to give 8.85 g. of the product, mp 273° C., decomposed.

Analyzed for $C_{18}H_{17}Br_2N_5$: Theoretical; C=46.80, H=3.71, N=15.12 Found; C=47.19, H=3.83, N=14.98.

EXAMPLE XXIV (1,3-Dimethyl-5-pyrazolyl) thiourea 1,3-Dimethyl-5-amino pyrazole (111.0 g.) and benzoyl iso thiocyanate (180.0 g.) were reacted as described in Example IV to give 110.3 g. of the product, mp 221°–224° C.

EXAMPLE XXV

N(1,3-Dimethyl-5-pyrazolyl)-S-methyl isothiourea hydroiodide (1,3-Dimethyl-5-pyrazolyl) thiourea (17.0 g) and 14.2 g methyl iodide were reacted as described in Example V to give 18.0 g. of the product, mp 158°–161° C.

Analyzed for $C_7H_{13}IN_4S$: Theoretical; C=26.92, H=4.16, N=17.94 Found; C=27.20, H=4.31, N=18.07.

EXAMPLE XXVI

2(1,3-Dimethyl-5-pyrazolyl) amino-b 2-imidazoline

N-(1,3-Dimethyl-5-pyrazolo)-S-methyl isothiourea hydroiodide (18.0 g.) and ethylene diamine (7.0 g.) were reacted as described in Example VI to give 7.60 g. of the product, mp 167°–169° C.

Analyzed for $C_8H_{13}N_5$: Theoretical; C=53.63, H=7.26, N=39.10 Found; C=53.58, H=7.36, N=39.11.

EXAMPLE XXVII

2(4-Bromo-1,3-dimethyl-5-pyrazolyl)-amino-2-imidazoline

2(1,3-Dimethyl-5-pyrazolyl)amino-2-imidazoline (13.25 g.) was treated with 12.8 g. bromine as described in Example III. The product was isolated as the base, 16.15 g. mp 230°–232° C.

Analyzed for $C_8H_{12}BrN_5$: Theoretical; C=37.21, H=4.65, N=27.13 Found; C=37.35, H=4.69, N=26.92.

EXAMPLE XXVIII

2(1,3-Dimethyl-4-iodo-5-pyrazolyl)-amino-2-imidazoline

2(1,3-Dimethyl-5-pyrazolyl) amino-2-imidazoline (8.95 g.) and 13.86 g. iodine was dissolved in 100 ml. acetic acid and stirred 16 hrs. at room temperature. The acetic acid was evaporated and sodium carbonate in water was added. The resulting solid was washed with water, and sodium sulfite solution and then crystallized from methanol to yield 6.85 g. of product, mp 226°–227° C.

Analyzed for $C_8H_{12}IN_5$: Theoretical; C=31.48, H=3.93, N=22.95 Found; C=31.37, H=3.98, N=23.10.

EXAMPLE XXIX

4-Amino-5-chloro-1,3-dimethyl pyrazole hydrochloride

4-Chloro-1,3-dimethyl-4-nitropyrazole (described in U.S. Pat. No. 3,282,954) (70.0 g.) was dissolved in 900 ml. methanol and 68 ml. concentrated HCl and hydrogenated over 3.2 g. platinum on carbon. After the hydrogen uptake ceased, the catalyst was filtered, the solvent concentrated in vacuum and the residue crystallized from isopropyl alcohol to get 64.15 g. of product, mp 234°–235° C., decomposed.

Analyzed for $C_5H_9Cl_2N_3$: Theoretical; C=32.99, H=4.98, N=23.08, Cl=38.95 Found; C=32.95, H=5.04, N=22.93, Cl=38.72.

EXAMPLE XXX

2-(4-chloro-1,3-dimethyl-4-pyrazolyl)-amino-2-imidazoline hydrochloride 4-amino-5-chloro-1,3-dimethylpyrazole hydrochloride (10.0 g.) in 10 ml. water was treated with 7.0 g. $KHCO_3$ and 200 ml. ether. After stirring the aqueous phase was extracted with benzene and the combined organic phases were dried over $MgSO_4$, concentrated and the residue was dissolved in 20 ml. methylene chloride.

2-chloro-2-imidazoline sulfate (J. Het. Chem. 1974 260) (16.64 g.) was converted to the free-base with $Na_2CO_3$ and extracted into methylene chloride. The amine solution above was added and the solution kept at 40° C. for 10 minutes, 30° C. for 1 hr. and refluxed 10 minutes. The solution was filtered and the filtrate concentrated. The residue was crystallized from isopropyl alcohol and ether to give 7.68 g. of product, mp 198°–200° C.

Analyzed for $C_8H_{13}Cl_2N_5$: Theoretical; C=38.41, H=5.24, N=28.00 Found; C=38.35, H=5.39, N=27.67

EXAMPLE XXXI

1-acetyl-2-(5-chloro-1,3-dimethyl-4-pyrazolyl) amino-2-imidazoline hydrochloride 4-amino-5-chloro-1,3-dimethyl pyrazole hydrochloride (12.8 g.) and 1-acetyl-2-imidazolidinone (10.0 g.) were reacted as described in Example I except the methylene chloride extract was not completely neutralized. The hydrochloride salt (6.42 g.) mp 215°–218° C., crystallized out at that point.

Analyzed for $C_{10}H_{15}Cl_2N_5O$: $H_2O$: Theoretical; C=39.90, H=5.64, N=22.25, Cl=23.58 Found; C=39.96, H=5.47, N=22.86, Cl=23.55.

The anti-inflammatory activity of the compounds of this invention was established using the reverse passive Arthus reaction in the rat as described by G. W. Carter and R. A. Krause in Federation Proceedings, Vol. 35, p. 774, 1976. The carrageenin rat paw edema test (Winter et al, Proc. Soc. Exp. Biol. Med., 111, 554, 1962) can be used to establish anti-inflammatory activity, however, unlike carrageenin induced edema, the Arthus reaction is a well characterized immune reaction which bears close resemblance to the pathogenisis of rheumatoid arthritis.

The Arthus reaction represents one of the oldest and best studied models of immunological injury. It is produced by the injection of antigen locally into a hyperimmunized animal or by the injection of a small amount of antibody into the skin of an animal that has just previously been given a large amount of soluble antigen intravenously. In both cases the antigen and antibody become deposited in the walls of small venules. Plasma complement is rapidly bound and activated. Within a few hours neutrophils (PMNs) accumulate, resulting in disruption of the basement membrane of vessel walls and marked edema and hemorrage in the surrounding tissue.

Although, the etiology of Rheumatoid arthritis remains obscure, it is almost certain that immunological mechanisms play an important role in the pathogenesis of this disease. Therefore, inflammation induced by immunological reactions, which are believed to be important in the inflammatory processes of rheumatoid arthritis, make particularly desirable tools for the screening of potential anti-inflammatory agents. The usefulness of such a model depends upon how closely it represents the underlying pathological mechanisms of rheumatoid arthritis.

Based upon currently available evidence, a plausible sequence of events leading to the joint leisions in rheumatoid arthritis can be constructed. An initiating antigen, perhaps a transient synovial infection, results in an immune response and retention of the antigen within the joint structure. The interaction of antigen with developing antibodies results in the deposition of immune complexes. These complexes may fix and activate complement, causing the generation of a number of phlogistic and chemotactic substances. Phagocytosis of the complexes by attracted polymorphonuclear leukocytes (PMNs) leads to the release of lysosomal constituents. The enzymes released from lysosomes can erode articular cartilage and produce inflammation in the joint. The striking resemblance of these events to the Arthus phenomenon point to the utility of the Arthus reaction as a screen for anti-inflammatory compounds.

The reverse passive Arthus reaction test in rats is conducted as follows. Male Sprague-Dawley rats weighing approximately 130–160 g. are used, 4 rats per group. All animals are injected intravenously with 0.5 ml. 0.075% Bovine Serum Albumin (B.S.A.)+0.2% Evans Blue solution. Each rat then receives an oral dose of drug; one drug is administered per group.

Thirty minutes subsequent to drug dosing, each animal is injected intradermally with 0.05 ml. 1.44% Anti-B.S.A. into the dorsal skin. Four hours later the animals are sacrificed, the dorsal skin reflexed, and the lesion excised. Two perpendicular diameters of each lesion are measured. The average diameters of the lesions from the treated groups are compared with the average diameters from the control group to determine any drug effect.

The anti-inflammatory activity of representative compounds of this invention, as determined by the reverse passive Arthus reaction test in rats, is summarized in Table I.

TABLE I

Anti-Inflammatory Effect of Compounds of Formula A in the Reverse Passive Arthus Reaction Test in Rats

| $R^1$ | $R^2$ | $R^3$ | $R^4$ | Percent Inhibition of Arthus Reaction (oral dose mg/kg) |
|---|---|---|---|---|
| $Me_2CH$ | Me | Br | H | 2:0% (100 mg/kg) |
| $Me_2CH$ | Me | H | H | 20% (50 mg) 29% (100 mg) |
| $Me_2CHCH_2-CH_2$ | Me | Br | H | 16% (100 mg) |
|  | | H | Br | H | 15% (100 mg) |

TABLE I-continued
Anti-Inflammatory Effect of Compounds of Formula A in the Reverse Passive Arthus Reaction Test in Rats

| $R^1$ | $R^2$ | $R^3$ | $R^4$ | Percent Inhibition of Arthus Reaction (oral dose mg/kg) |
|---|---|---|---|---|
| Me | $Me_2CH$ | Br | H | 37% (50 mg) 42% (100 mg) |
| $Me_2CH-CH_2-CH_2$ | Me | H | H | 15% (100 mg) |
| Me | $Me_2CH$ | H | H | 33% (50 mg) 42% (100 mg) |
| ⟨S⟩- | H | H | H | 15% (100 mg) |
| $Me_2CH$ | $Me_2CH$ | Br | H | 27% (100 mg) |
| $Me_2CH$ | $Me_2CH$ | H | H | 11% (100 mg) |
| $C_6H_5$ | H | Br | H | 41% (25 mg) 59% (100 mg) |
| $C_6H_5$ | H | H | H | 62% (25 mg) 75% (100 mg) |
| $C_6H_5$ | $C_6H_5$ | Br | H | 17% (100 mg) |
| $C_6H_5$ | $C_6H_5$ | H | H | 32% (100 mg) |
| Me | Me | I | H | 43% (100 mg) |
| Me | Me | Br | H | 45% (50 mg) |
| Me | Me | H | H | 55% (100 mg) |
| $C_6H_5$ | H | H | $COCH_3$ | 70% (100 mg) |
| $Me_2CH$ | Me | H | $COCH_3$ | 30% (50 mg) 39% (100 mg) |
| Me | $Me_2CH$ | H | $COCH_3$ | 18% (100 mg) |
| Me | Me | (5) Cl | $COCH_3$ | 39% (25 mg) 63% (100 mg) |
| Me | Me | (5) (Cl) | H | 49% (10 mg) 64% (25 mg) 69% (100 mg) |

Note: Me represents $CH_3$. The $R^3$ substituent is located in the 4 position unless otherwise noted.

The compounds of the present invention can be incorporated into pharmaceutically acceptable dosage forms such as suspensions, tablets, capsules, and the like for either immediate or sustained release. By combining them with suitable carriers or diluents using conventional methods known in the art. In addition to the active agent and the carrier or diluent, the dosage forms may include various binders, excipients, fillers, or flavoring agents to provide a satisfactory formulation of the desired pharmaceutical preparation.

What is claimed is:

1. A compound represented by the structural formula

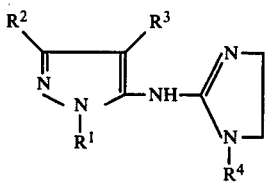

wherein $R^1$ and $R^2$ are each hydrogen, $C_1-C_6$ alkyl, cycloalkyl up to 6 carbon atoms or phenyl, $R^3$ is hydrogen or halogen, $R^4$ is hydrogen or acetyl, and pharmaceutically acceptable acid addition salts thereof.

2. A compound represented by the structural formula

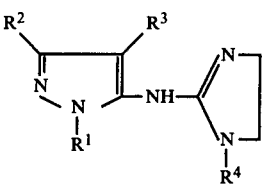

wherein $R^1$ and $R^2$ are each hydrogen, $C_1-C_6$ alkyl or phenyl, $R^3$ is hydrogen, chloro, bromo or iodo, and $R^4$ is hydrogen or acetyl, and pharmaceutically acceptable acid addition salts thereof.

3. A compound of claim 2 wherein $R^1$ is methyl or phenyl, $R^2$ is hydrogen, methyl, or propyl, $R^3$ is hydrogen chloro, bromo, or iodo, and $R^4$ is hydrogen or acetyl.

4. A compound of claim 3 wherein $R^1$ is phenyl, and $R^2$, $R^3$ and $R^4$ are each hydrogen.

5. A compound of claim 3 wherein $R^1$ is methyl, $R^2$ is methyl, $R^3$ is chloro, and $R^4$ is hydrogen, and the hydrochloride salt thereof.

6. A compound of claim 3 wherein $R^1$ is methyl, $R^2$ is methyl, $R^3$ is chloro, and $R^4$ is acetyl, and the hydrochloride salt thereof.

7. A compound of claim 3 wherein $R^1$ is phenyl, $R^2$ is hydrogen, $R^3$ is hydrogen, and $R^4$ is acetyl.

8. A pharmaceutical composition for treating inflammation comprising as the essential active ingredient an effective amount of a compound represented by the structural formula

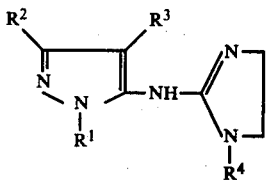

wherein $R^1$ and $R^2$ are each hydrogen, $C_1-C_6$ alkyl, cycloalkyl up to 6 carbon atoms or phenyl, $R^3$ is hydrogen or halogen, $R^4$ is hydrogen or acetyl, or a pharmaceutically acceptable acid addition salt thereof in admixture with a pharmaceutically acceptable carrier.

9. A composition of claim 8 wherein $R^1$ is methyl or phenyl, $R^2$ is hydrogen, methyl, or propyl, $R^3$ is hydrogen, chloro, bromo, or iodo, and $R^4$ is hydrogen or acetyl.

10. A composition of claim 9 wherein the amount of said essential active ingredient is from about 5 mg. to 200 mg. in terms of dosage unit per day per kilogram of body weight.

11. A method of treating inflammation in mammalian patients in need of such treatment which comprises administering to said patients an effective amount of a compound represented by the structural formula

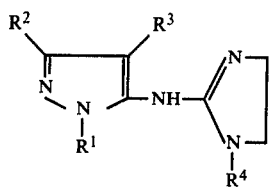

wherein $R^1$ and $R^2$ are each hydrogen, $C_1$–$C_6$ alkyl, cycloalkyl up to 6 carbon atoms or phenyl, $R^3$ is hydrogen or halogen, $R^4$ is hydrogen or acetyl or a pharmaceutically acceptable acid addition salt thereof, either alone or in admixture with a pharmaceutically acceptable carrier.

12. The method of claim 11 wherein said compound or pharmaceutically acceptable acid addition salt thereof is orally administered in an amount of from about 5 mg. to 200 mg. per kilogram of body weight per day.

* * * * *